(12) United States Patent
Urich et al.

(10) Patent No.: US 8,511,581 B2
(45) Date of Patent: *Aug. 20, 2013

(54) FLUID DROPLET PRODUCTION APPARATUS AND METHOD

(75) Inventors: Markus Urich, Munich (DE); Samuel Charles William Hyde, Cambridge (GB); Neil Pollock, Royston (GB); Andrew Jonathan Sant, Cambridge (GB)

(73) Assignee: PARI Pharma GmbH, Starnberg (DE)

( * ) Notice: Subject to any disclaimer, the term of this patent is extended or adjusted under 35 U.S.C. 154(b) by 100 days.

This patent is subject to a terminal disclaimer.

(21) Appl. No.: 13/042,980

(22) Filed: Mar. 8, 2011

(65) Prior Publication Data

US 2011/0155768 A1    Jun. 30, 2011

Related U.S. Application Data

(63) Continuation of application No. 10/522,344, filed as application No. PCT/EP03/08482 on Jul. 31, 2003, now Pat. No. 7,931,212.

(30) Foreign Application Priority Data

Aug. 2, 2002    (EP) .................................... 02016972

(51) Int. Cl.
*B05B 3/04*          (2006.01)
*B05B 1/08*          (2006.01)

(52) U.S. Cl.
USPC ..................... 239/102.1; 239/102.2; 239/552; 239/556; 239/596; 239/602

(58) Field of Classification Search
USPC ................... 239/102.1, 102.2, 552, 556, 596, 239/602
See application file for complete search history.

(56) References Cited

U.S. PATENT DOCUMENTS

| | | | |
|---|---|---|---|
| 3,400,892 A | 9/1968 | Ensminger | |
| 3,747,914 A | 7/1973 | Thrasher | |
| 3,790,079 A | 2/1974 | Berglund et al. | |
| 3,812,854 A | 5/1974 | Michaels et al. | |
| 4,081,233 A | 3/1978 | Kitajima et al. | |

(Continued)

FOREIGN PATENT DOCUMENTS

| EP | 0615470 B1 | | 9/1994 |
|---|---|---|---|
| EP | 1214986 | * | 6/2002 |

(Continued)

OTHER PUBLICATIONS

Maehara et al., "*Influence of the Vibrating System of a Multipinhole-Plate Ultrasonic Nebulizer on its Performance*," Rev. Sci. Instrum. 57(11), Nov. 1986, pp. 2870-2876.

(Continued)

*Primary Examiner* — Dinh Q Nguyen
(74) *Attorney, Agent, or Firm* — Wolf, Greenfield & Sacks, P.C.

(57) ABSTRACT

A fluid dispersion device comprises a substrate having an outer section and an inner section, said inner section of the substrate having an aperture, a dispersion element positioned at said aperture of said substrate, and an actuator arranged to coaxially surround said aperture of said substrate, wherein the outer edge of said inner section of said substrate is coupled to said outer section of said substrate by a plurality of resilient members.

18 Claims, 10 Drawing Sheets

(56) References Cited

U.S. PATENT DOCUMENTS

Figure 1A:
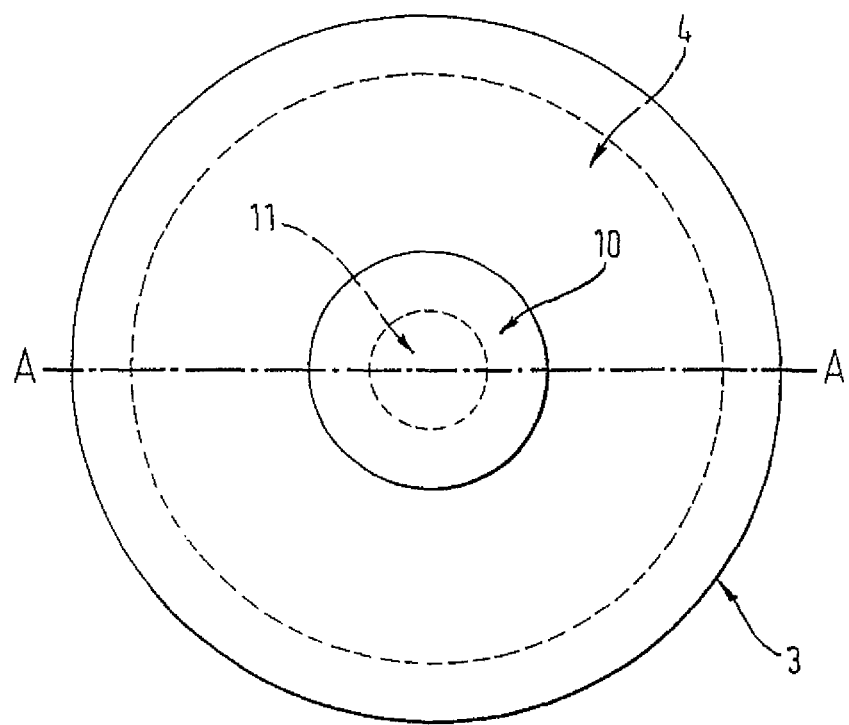

| | | |
|---|---|---|
| 4,165,961 A | 8/1979 | Yamamoto et al. |
| 4,429,247 A | 1/1984 | Feldman |
| 4,465,234 A | 8/1984 | Maehara et al. |
| 4,482,124 A | 11/1984 | Dochterman |
| 4,530,464 A | 7/1985 | Yamamoto et al. |
| 4,533,082 A | 8/1985 | Maehara et al. |
| 4,632,311 A | 12/1986 | Nakane et al. |
| 4,790,482 A | 12/1988 | Won |
| 5,152,456 A | 10/1992 | Ross et al. |
| 5,261,601 A | 11/1993 | Ross et al. |
| 5,310,157 A | 5/1994 | Platus |
| 5,518,179 A | 5/1996 | Humberstone et al. |
| 5,586,550 A | 12/1996 | Ivri et al. |
| 5,657,926 A | 8/1997 | Toda |
| 5,938,117 A | 8/1999 | Ivri |
| 6,378,780 B1 | 4/2002 | Martens et al. |
| 6,467,476 B1 | 10/2002 | Ivri et al. |
| 6,554,201 B2 | 4/2003 | Klimowicz et al. |
| 6,629,646 B1 | 10/2003 | Ivri |
| 6,732,944 B2 | 5/2004 | Litherland et al. |
| 6,814,071 B2 | 11/2004 | Klimowicz et al. |
| 6,978,941 B2 | 12/2005 | Litherland et al. |
| 7,104,463 B2 * | 9/2006 | Litherland et al. ............ 239/4 |
| 7,607,589 B2 * | 10/2009 | Yu et al. .................. 239/102.2 |
| 2002/0162551 A1 | 11/2002 | Litherland |
| 2006/0011737 A1 * | 1/2006 | Amenos et al. ............ 239/102.1 |
| 2006/0097068 A1 | 5/2006 | Urich et al. |

FOREIGN PATENT DOCUMENTS

| | | |
|---|---|---|
| EP | 1214986 A1 | 6/2002 |
| FR | 2348058 | 4/1976 |
| GB | 2 263 076 A | 7/1993 |
| JP | 59-032971 | 2/1984 |
| JP | 60-175566 | 9/1985 |
| WO | WO 92/11050 | 7/1992 |
| WO | WO 02/087774 A1 | 11/2002 |

OTHER PUBLICATIONS

Reid et al., "*A Micromachined Vibration Isolation system for Reducing the Vibration Sensitivity of Surface Transverse Wave Resonators,*" IEEE Transactions on Ultrasonics, Ferroelectrics, and Frequency Control, vol. 45, No. 2, Mar. 1998, pp. 528-534.

Ueha et al., "*Mechanism of ultrasonic atomization using a multi-pinhole plate,*" J. Acoust. Soc. Jpn. (E)6, 1 (1985) pp. 21-26.

Search Report mailed Jul. 12, 2002 from International Application No. PCT/US02/14208.

Search Report mailed Dec. 17, 2003 from corresponding International Application No. PCT/EP03/08482.

International Preliminary Examination Report completed on Jun. 2, 2004 from corresponding International Application No. PCT/EP03/08482.

* cited by examiner

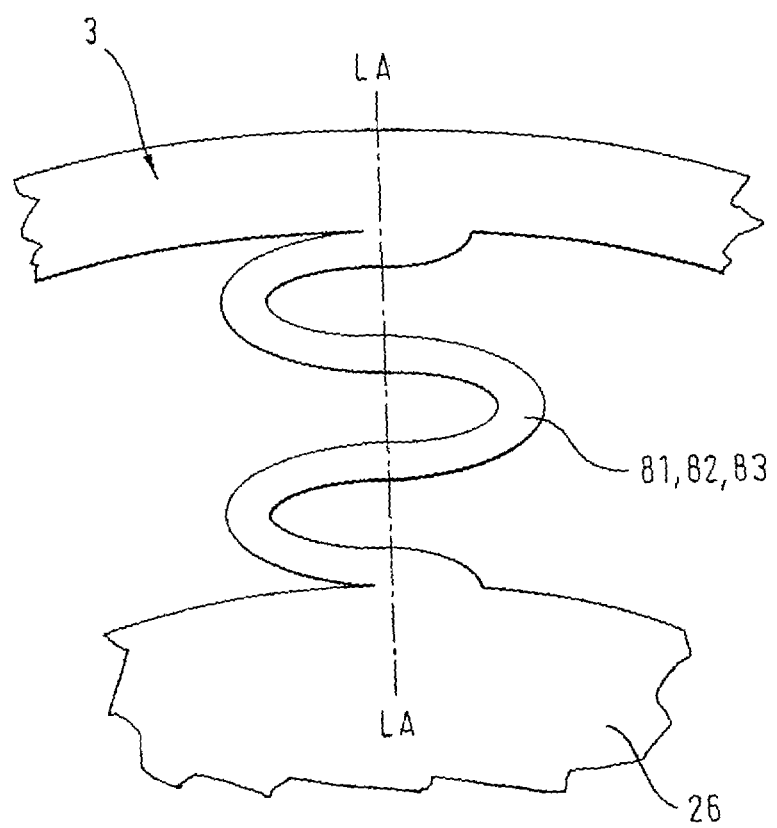

FLUID DROPLET PRODUCTION APPARATUS AND METHOD

CROSS REFERENCE TO RELATED APPLICATION

This application is a continuation of U.S. patent application Ser. No. 10/522,344, filed Aug. 25, 2005, which is a national phase of International Application No. PCT/EP2003/008482, filed Jul. 31, 2003, which claims priority based on European Patent Application No. 02016972.8, filed Aug. 2, 2002, which are hereby incorporated by reference in their entirety.

BACKGROUND OF THE INVENTION

In a variety of industrial fields, for example those involved in the manufacturing of devices for the administration of medicinal compounds, it is desirable to find means for nebulising a fluid or liquid in a controlled manner.

One known solution to this problem involves the agitation of a membrane by means of a piezoelectric oscillator, wherein the fluid to be nebulised is placed at one side of said membrane such that the fluid is nebulised in a controlled manner to provide fine liquid droplet sprays, mists or aerosols on the other side of the membrane.

Figure 1B:
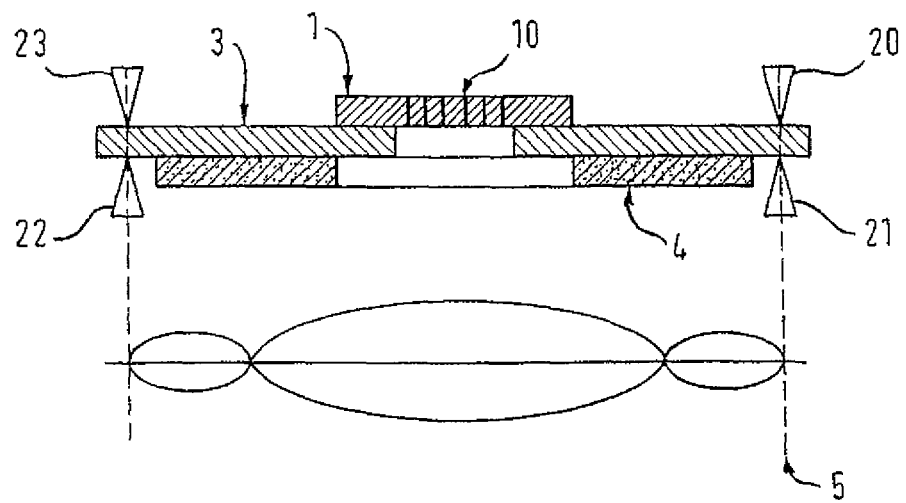
Figure 1C:
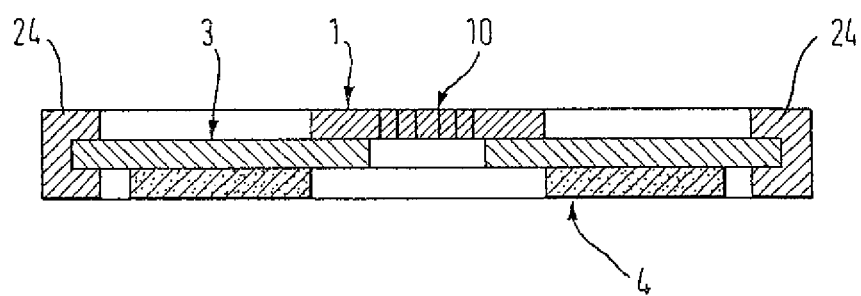

Such a device, as for example known from EP 0 615 470 A, commonly comprises an annular substrate, on one side of which is disposed an annular piezoelectric device, and on the other side of which is placed a circular dispersion element, all three elements being disposed coaxially. The circular dispersion element may comprise a plurality of fine diameter holes, substantially parallel to the axis of the device, through which fluid passes to form droplets. A device of this kind is shown in FIG. 1A, while FIG. 1B shows a cross-section of the device of 1A along the lines of AA and how on the energizing of the piezoelectric element 4, a standing wave is set up through the device as a whole, having maxima at the centre of the device, where the dispersion element or mesh 10 is located, and side lobes nearer the circumference of the substrate.

A problem arises with the described device where it is necessary to fixedly attach it to a housing. The ways of doing this known in the prior art either result in an undesirable influence on the oscillation characteristics of the device or are difficult to handle, especially in the case of a medical treatment device employing such a device.

One known method of securing the nebuliser known in the prior art, as indicated in FIG. 1B, involves the provision of bearings 20, 21, 22 and 23 positioned so as to support the substrate 3 at points at which the standing wave present under oscillating conditions is known to be a minimum. Clearly, this solution is limited by practical considerations, such that in practice a significant deterioration in the performance of the nebuliser is experienced.

An alternative method known in the prior art, as indicated in FIG. 1C, involves the clamping of the substrate 3 at an circumferential edge, involving using fixed clamps 24. Once again, this results in a significant deterioration in the performance in the nebuliser. If the clamping is achieved by means of a ring of a soft resilient material the small gaps between the ring 24 an the substrate 3 are prone to collect fluids or other substances causing hygiene problems.

As mentioned above, these and other prior art methods of fixedly securing the nebuliser device are disclosed in EP 0 615 470 A.

A further problem arising in these known techniques is that there are provided numerous devices which are prone to retention of stray matter in an undesirable manner, particularly in medical applications where hygiene is of particular importance.

SUMMARY OF THE INVENTION

According to the present invention from a first aspect there is provided a fluid dispersion device comprising a fixed frame 25, a substrate 3 having a central aperture 11, a dispersion element 10 positioned over said central aperture 11 of said substrate 3, and an annular actuator 4 arranged coaxially with said central aperture 11 of said substrate 3, wherein the outer edge of said substrate 3 is coupled to said fixed frame 25 by a plurality of resilient members 81, 82, 83.

According to a development of this first aspect of the invention, said plurality of resilient members 81, 82, 83 are serpentine in form.

According to a further development of this first aspect of the invention, said plurality of resilient members 81, 82, 83 are aligned radially about the axis of said central aperture 11 of said substrate 3.

According to a further development of this first aspect of the invention, said plurality of resilient members 81, 82, 83 are aligned at an angle to a line radiating from the centre of said central aperture 11 of said substrate 3.

According to a further development of this first aspect of the invention, said substrate 3, said fixed frame 25 and said resilient members 81, 82, 83 are formed as a single solid.

According to a further development of this first aspect of the invention, said annular actuator 4 is a piezoelectric device.

According to a further development of this first aspect of the invention, at least one of said resilient members 81, 82, 83 is disposed so as to carry an electronic signal to said annular actuator 4.

BRIEF DESCRIPTION OF THE DRAWINGS

The present invention will now be described in more detail by reference to the following figures.

FIG. 1A shows a plan view of a nebulising device as known in the prior art.

FIG. 1B shows a cross-section of the nebulising device as known in the prior art secured in a first manner and how a standing wave exists in the nebulising device in operation.

FIG. 1C shows a cross-section of the nebulising device as known in the prior art secured in a second manner.

FIG. 2A shows a plan view of a nebuliser according to a first embodiment of the present invention.

FIG. 2B shows a cross-section of the nebuliser of FIG. 2A.

FIG. 3A shows a plan view of a nebuliser according to a second embodiment of the present invention.

FIG. 3B shows a cross-section of the nebuliser of FIG. 3A.

FIG. 4A shows a plan view of a nebuliser according to a third embodiment of the present invention.

FIG. 4B shows a cross-section of the nebuliser of FIG. 4A.

FIG. 5 shows an example of a meandering/serpentine resilient member according to the invention.

FIG. 6 shows another example of a meandering/serpentine resilient member according to the invention.

FIG. 7 shows another example of the fluid dispersion device according to the invention having a non-meandering resilient member.

FIG. 8 shows another embodiment of the fluid dispersion device according to the invention having attachment sections.

FIG. 9 shows another embodiment of the fluid dispersion device according to the invention having outer partial section supported in a supporting structure.

DETAILED DESCRIPTION

In the following, a fluid dispersion device according to the invention will be described in detail with reference to FIGS. 2 to 8, said device comprising a substrate 3 having an outer section 25 and an inner section 26, said inner section 26 of the substrate 3 having an aperture 11, a dispersion element 10 positioned at said aperture 11 of said substrate 3 to cover the aperture, and an actuator 4 arranged to surround said aperture 11 of said substrate 3, wherein the outer edge of said inner section 26 of said substrate 3 is coupled to said outer section 25 of said substrate 3 by a plurality of resilient members 81, 82, 83.

Figure 2A:
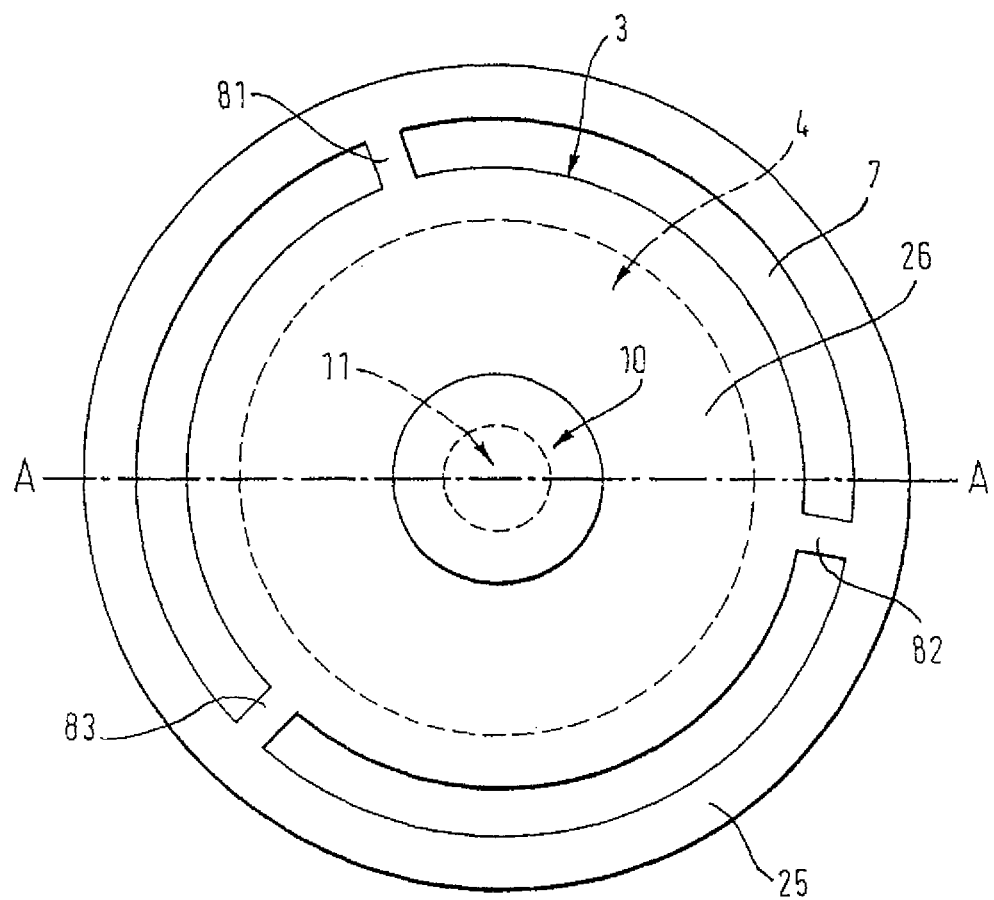
Figure 2B:
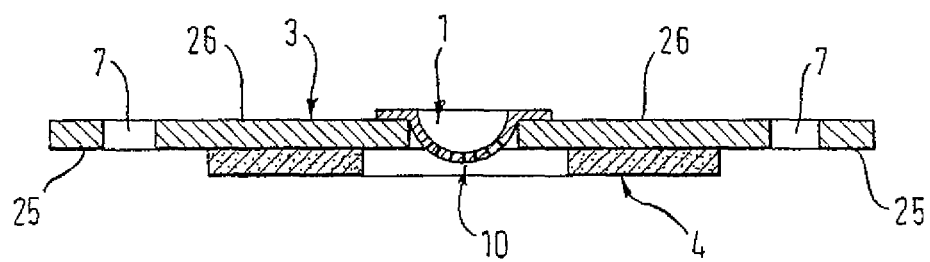

According to a first embodiment of the present invention, as shown in FIGS. 2A and 2B, there is provided a nebulising arrangement comprising a substrate 3, a piezoelectric element 4, and a nebulising element 1. The piezoelectric element 4 is annular in shape, while the substrate 3 comprises openings so as to form an inner annular section 26 and an outer annular section 25, these two annular sections being connected, preferably in the same plane, by a plurality of connecting spoke elements 81, 82 and 83. The piezoelectric element 4 is attached to one side of the inner annular section 26 of the substrate 3, and is arranged coaxially therewith. Similarly, the nebulising element 1 is disposed on the opposite side of inner annular section 26 of the substrate 3, and coaxially with said substrate 3 and piezoelectric element 4, so as to cover the opening in the center of the inner annular section 26 of the substrate 3. The nebulising element 1 may also be provided on the same side of the substrate 3 as the piezoelectric element 4 or may be formed as one piece with said substrate 3 by thinning the substrate 3 at the area defined by said aperture and by providing fluid passage ways through the thinned portion of the substrate.

The dispersion element 1 is preferably dome shaped, as shown in FIG. 2B, or may be substantially flat. Further, if the liquid is provided on one side of the dispersion element and the fine droplet spray is to be generated on the other side, the dispersion element 1 is provided with fine holes or openings 10 to allow the liquid to pass.

The outer annular section 25 of the nebulising device according to the invention may be fixed or clamped to a housing (not shown) as known in the prior art, so as to be held substantially immobile with respect to the housing. By means of the connecting spoke elements 81, 82, 83 the inner annular section 26 is supported and thereby securely attached to the outer annular section 25.

In operation, an electrical signal is applied to the piezoelectric element 4 in an appropriate manner, for example through the inner section 26 of the substrate 3 and a further electrode disposed on the opposite side of the piezoelectric element 4. The electrical signal may be carried by at least one of the resilient members 81, 82, 83 to the inner section 26 and by the outer section 25 to the at least one resilient spoke element 81, 82, 83, respectively. By applying an appropriate electrical signal to the piezoelectric element 4, contractions and expansions of the piezoelectric element 4 are induced in a direction parallel to the plane of the substrate 3 causing an oscillation of the structure comprising the nebulising element 1, the inner annular section 26, and the piezoelectric element 4 as whole in a direction substantially perpendicular to said plane. By controlling the signal, not only the behavior of the piezoelectric element 4 but also the oscillation of the overall device is controlled, and thereby the generation of the fine droplet spray as well.

Since the inner annular section 26 is supported only via the connecting spoke elements 81, 82, 83, the deterioration in the performance of the nebulising device caused by its mounting structure, is substantially less than that experienced in the prior art, due to the resilience of the connecting spoke elements 81, 82, 83. The resilience characteristics of the connecting spoke elements 81, 82, 83 can easily be adapted by defining the shape, i.e. in the first embodiment the length, width and thickness of each resilient member 81, 82, 83. The resilience can further be influenced according to design requirements by selecting an appropriate material, for example, stainless steel etc.

The connecting spoke elements 81, 82, 83 according to the invention reduce the deteriorating influence of the support structure on the nebulising device due to the adaption of the resilience characteristics whereby the forces applied to those ends of the connecting spoke element which are attached to the inner annular section 26 are reflected from the other ends of the connecting spoke elements, i.e. which are attached to the outer annular section 26. The forces applied to the connecting spoke elements 81, 82, 83 due to the oscillation of the inner annular section 26 causes the adapted connecting spoke elements to oscillate in or near resonance such that a wave induced by the forces applied exhibits an oscillation node at the other end, i.e. the end attached to the outer annular section 25.

As mentioned above, the membrane or mesh 1, i.e. the dispersion element, may be a formed with a central dome as shown in FIGS. 2 to 4, or may be a flat disk, and may be formed of stainless steel, silver coated nickel or other suitable material. The dome may be formed by stamping or deep drawing a flat disk to form the desired shape.

The inner and the outer section 25, 26 of the substrate 3 and the resilient members 81, 82, 83 may be, for example, of stainless steel and may be formed as a solid or as individual components, also of different materials.

The membrane may, for example, be welded to the substrate, by means of a laser.

Figure 3A:
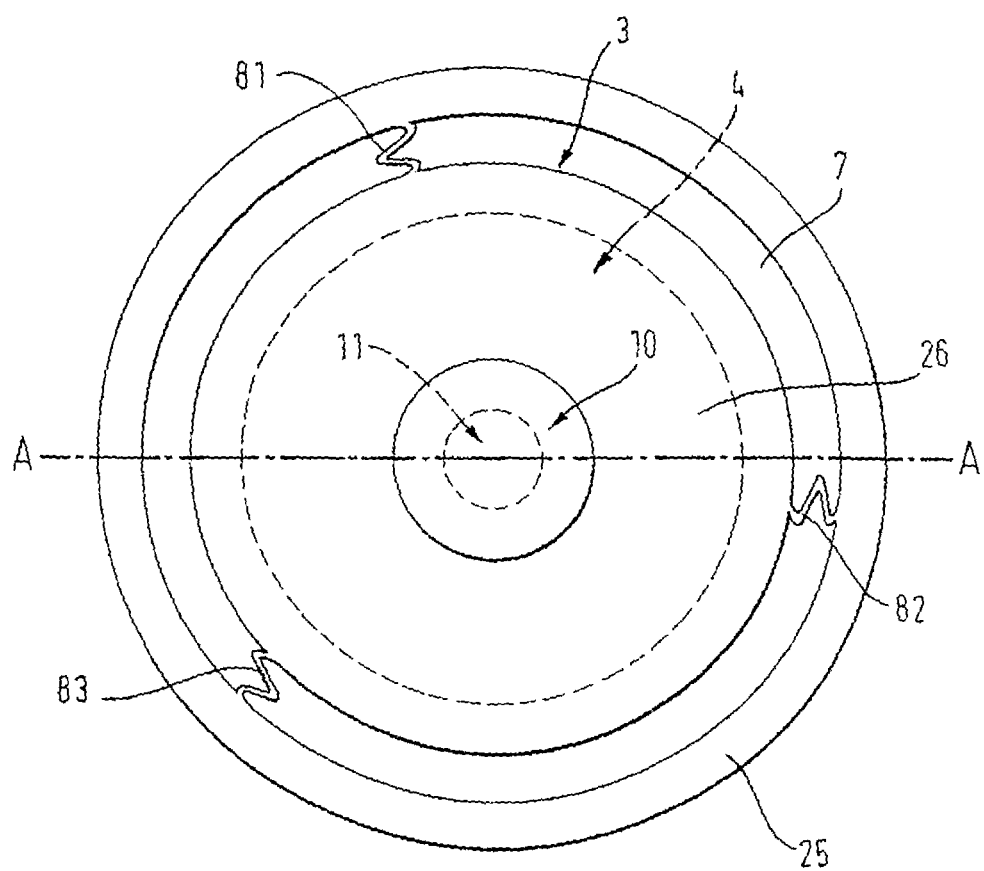
Figure 3B:
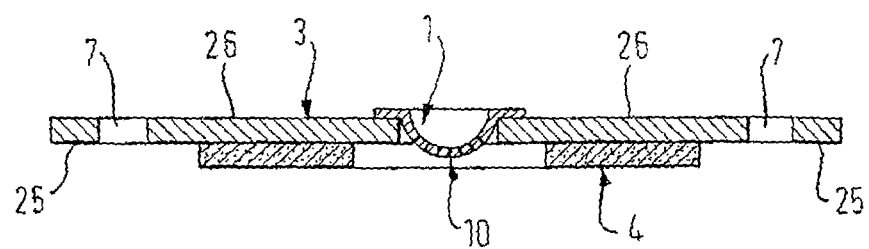

A second embodiment of the present invention is shown in FIGS. 3A and 3B. The nebulising device according to this embodiment is provided with all elements of the first embodiment, which are numbered correspondingly. The second embodiment differs from the first embodiment in that the connecting spoke elements 81, 82, 83 are formed as serpentine or meandering elements. By this means, the degree of influence of the mounting on the oscillations of the central arrangement, comprising at least the dispersion element 1, the inner section 26 of the substrate 3 and the actuator 4, is further reduced without an increase in the distance between the outer edge of the inner annular section of the substrate 3 and the inner edge of the outer annular section 25. Still the inner annular section 26 is safely supported similar to the first embodiment.

Figure 4A:
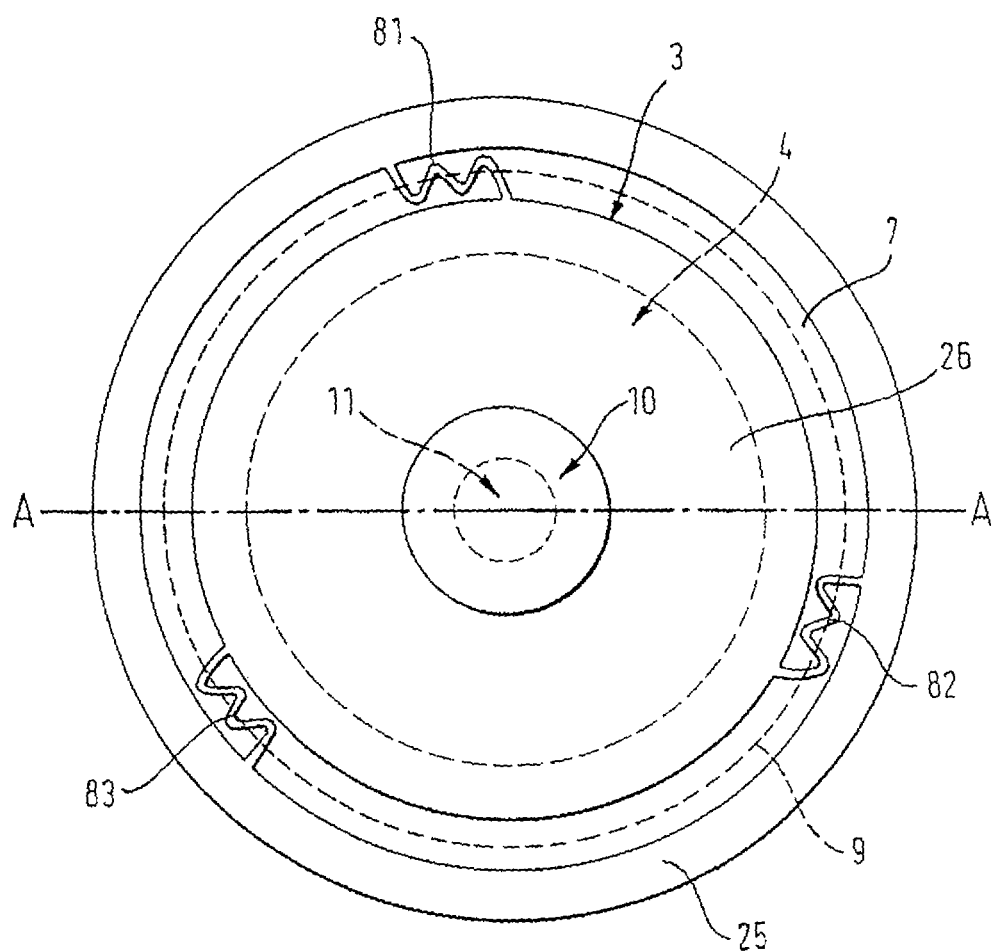
Figure 4B:
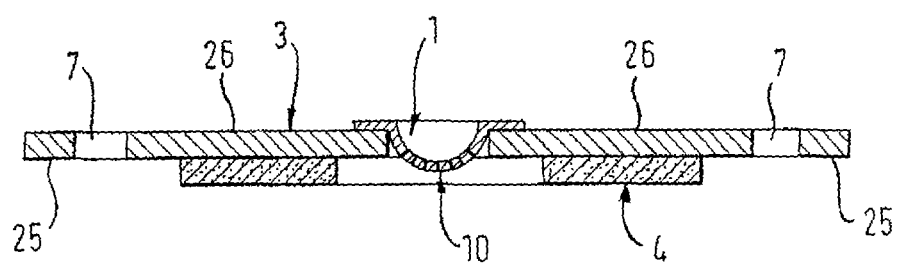

A third embodiment of the present invention is shown in FIGS. 4A and 4B. The nebulising device according to this embodiment is provided with all elements of the second embodiment, which are numbered correspondingly. The third embodiment differs from the second in that the connecting spoke elements 81, 82, 83 are formed as serpentine elements. In general, serpentine shaped elements can be defined with reference to a longitudinal axis LA as shown in FIG. 5. The example of FIG. 5 resembles the waveform of a sinusoidal wave and is asymmetrical as two maxima of the sinus wave are provided on one side of longitudinal axis LA and only a single maximum is provided on the other side. However, still within the scope of the present invention, a symmetrical arrangement of maxima on both sides of longitudinal axis LA may be provided. Also, any other serpentine or meandering shape may be employed for embodying the serpentine resilient elements according to the third embodiment of the invention.

Figure 6:
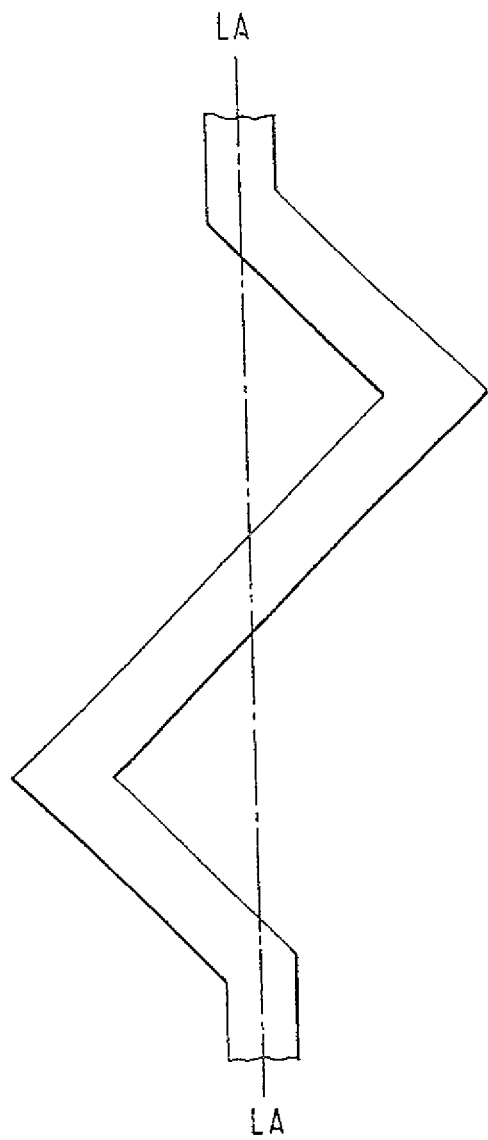

As a further example, FIG. 6 shows a serpentine resilient element being assembled by two triangular shaped sections of which one is provided on either side of longitudinal axis, respectively. Obviously, more than two triangular shaped sections may be provided. Also, rectangular shaped sections, semi circular shaped sections, saw-tooth shaped section, and any section of any other shape may be used. The individual section may be of different shape as well, so that, for example, a triangular shaped section may be followed by a rectangular shaped section. Again, as should be obvious, more than two sections may be combined to form a resilient element.

In FIGS. 5 and 6, the longitudinal axis LA is shown as a straight line. However, in general and also with respect to the third embodiment above, the longitudinal axis may be understood to be part of circle as shown as a dotted line in FIG. 4A. However, in view of the typical relationship between the radius of said circle and the length of the individual meandering resilient element, the longitudinal axis LA can be considered as a straight axis. This assumption has been used in the above description of the general shape of the meandering serpentine resilient elements according to the third embodiment of the invention with respect to FIGS. 5 and 6.

According to the invention and as shown in FIG. 4A, the meandering resilient elements 81, 82, 83 are disposed at an angle to a line radiating from the centre of said central aperture 11 of the substrate 3. If the angle is substantially equal to 90°, as shown in FIG. 4A, the ring shaped gap 7 between the inner annular section 26 and the outer annular section 25 of the substrate 3 is minimized. The longitudinal axis of each serpentine shaped connecting spoke element 81, 82, 83 is arranged substantially tangential to the circle 9 shown as a dotted line in FIG. 4A.

In other words, the serpentine elements are preferably disposed along a circular line 9 situated between the outer edge of the central portion 26 of the substrate 3 and the inner edge of the outer ring 25 and substantially concentric therewith. The two ends of each resilient element deviate from this line so as to join the outer edge of the inner portion 26 of the substrate 3 and the inner edge of the outer portion 25, respectively. By this means, the degree to which oscillations of the central portion 26 of the substrate 3 to which the piezoelectric element 4 is attached are negatively influenced by the mounting is reduced, with a minimum increase in the distance between the outer edge of the central portion 26 of the substrate 3, and the inner edge of the outer ring 25.

Figure 7:
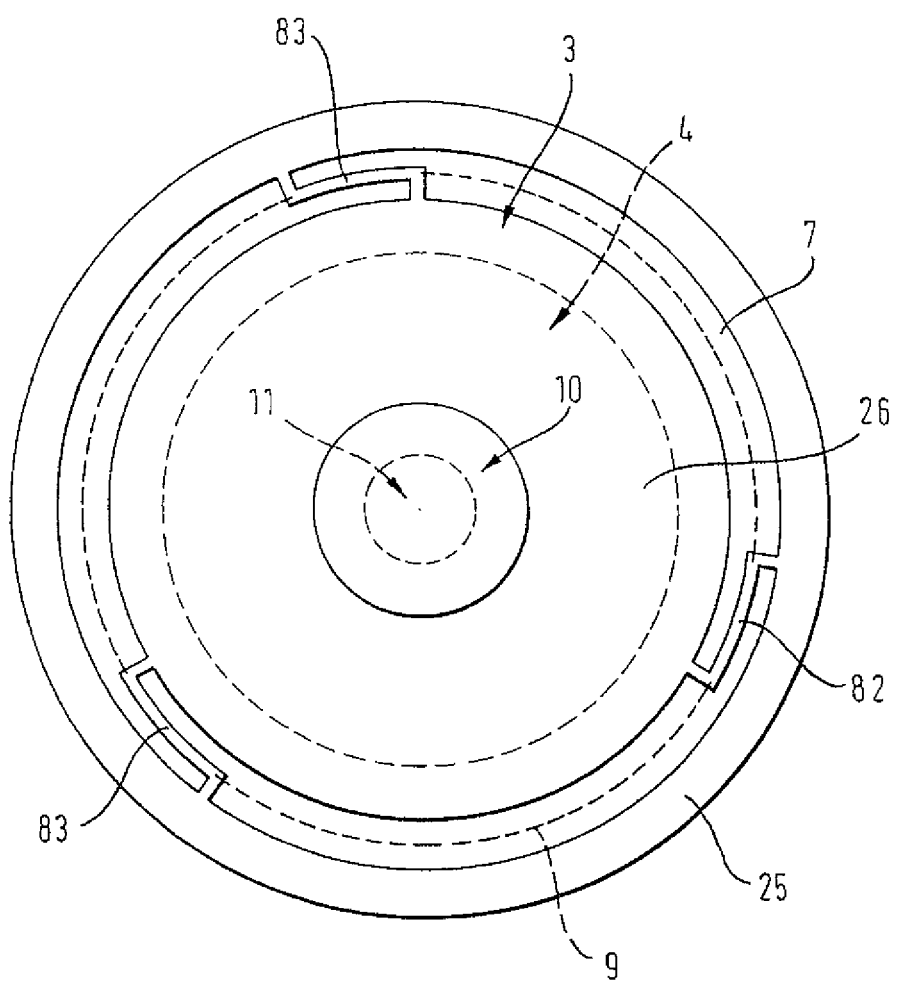

A fourth embodiment of the present invention is shown in FIG. 7. The nebulising device according to this embodiment is provided with many elements of the third embodiment, which are numbered correspondingly. The fourth embodiment differs from the third embodiment in that the connecting resilient elements 81, 82, 83 are formed as non-meandering resilient members. According to the invention and as shown in FIG. 7, the non-meandering resilient members 81, 82, 83 are disposed at an angle to a line radiating from the center of said central aperture 11 of the substrate 3. If the angle is substantially equal to 90°, as shown in FIG. 7, the ring shaped gap 7 between the inner annular section 26 and the outer annular section 25 of the substrate 3 is minimized. It should be noted that the gap 7 is in general smaller when non-meandering resilient members are used. Further, the non-meandering resilient members may be arc-shaped to extend substantially in parallel to the edges towards the gap of the inner and the outer annular section 26 and 25, respectively. It is preferable to arrange the longitudinal axis of each non-meandering connecting spoke element 81, 82, 83 substantially tangential to the circle 9 shown as a dotted line in FIG. 7.

In other words, the non-meandering elements are preferably disposed along a circular line 9 situated between the outer edge of the central portion 26 of the substrate 3 and the inner edge of the outer ring 25 and in a preferred embodiment substantially concentric therewith. The two ends of each resilient element deviate from this line so as to join the outer edge of the inner portion 26 of the substrate 3 and the inner edge of the outer portion 25, respectively. Thereby, the degree to which oscillations of the central portion 26 of the substrate 3 to which the piezoelectric element 4 is attached are negatively influenced by the mounting is reduced, with a minimum increase in the distance between the outer edge of the central portion 26 of the substrate 3, and the inner edge of the outer ring 25.

Figure 8:
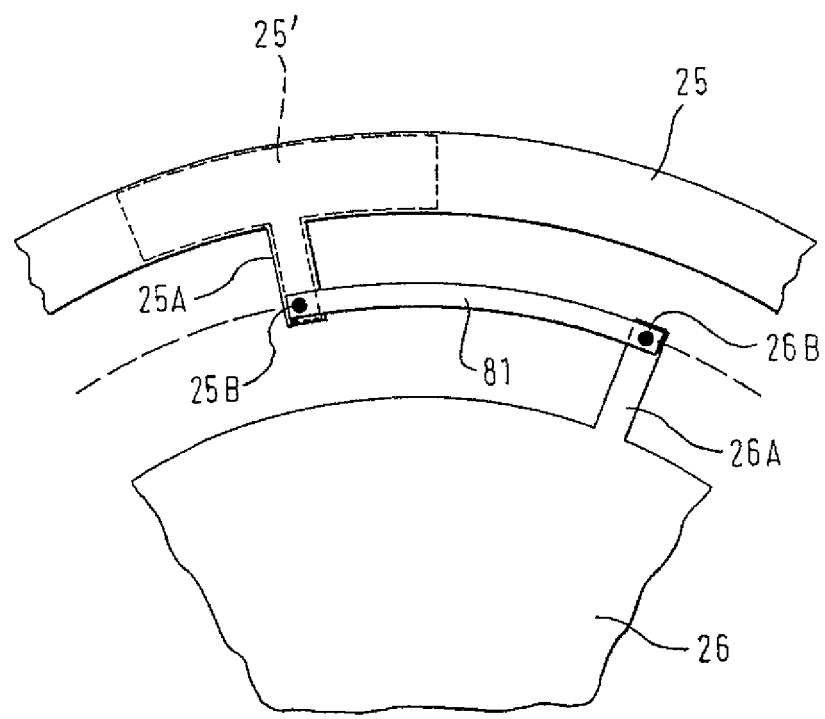

In order to facilitate manufacturing of the device according to the invention and also to further reduce the deteriorating effect caused by the mounting structure, the outer section 25 and the inner section 26 may be manufactured separately and the connecting spoke elements 81, of which only one is shown in FIG. 8 as an example, may be attached to corresponding attachment sections 25A provided integral with the outer section 25 of the substrate 3, as shown in FIG. 8. The connecting resilient spoke members 81 and the inner section 26 of the substrate 3 are advantageously manufactured as one piece. The attaching of the resilient elements 81 may be achieved by welding or otherwise at point 25B any time during the manufacturing process. Thereby, the manufacturing of the outer section 25 and its further supporting structure may be performed separately from the manufacturing of the inner section 26 and the resilient spoke elements 81.

Further, the inner section 26 may be provided with attachment sections 26A similar to the outer section 25. The resilient spoke elements 81 may be welded at welding point 26B or otherwise attached to the inner section 26. Thus, the resilient elements 81 may be manufactured separately from the inner and outer section of the substrate 3 so that the resilient elements 81 may be of a material different from the substrate 3.

Of course, the resilient members 81 may be formed in one piece with the outer section 25 of the substrate 3 and may be attached at attachment point 26B of an attachment section 26A of the inner section 26 of the substrate 3 in an appropriate step of the manufacturing process as described above.

Figure 9:
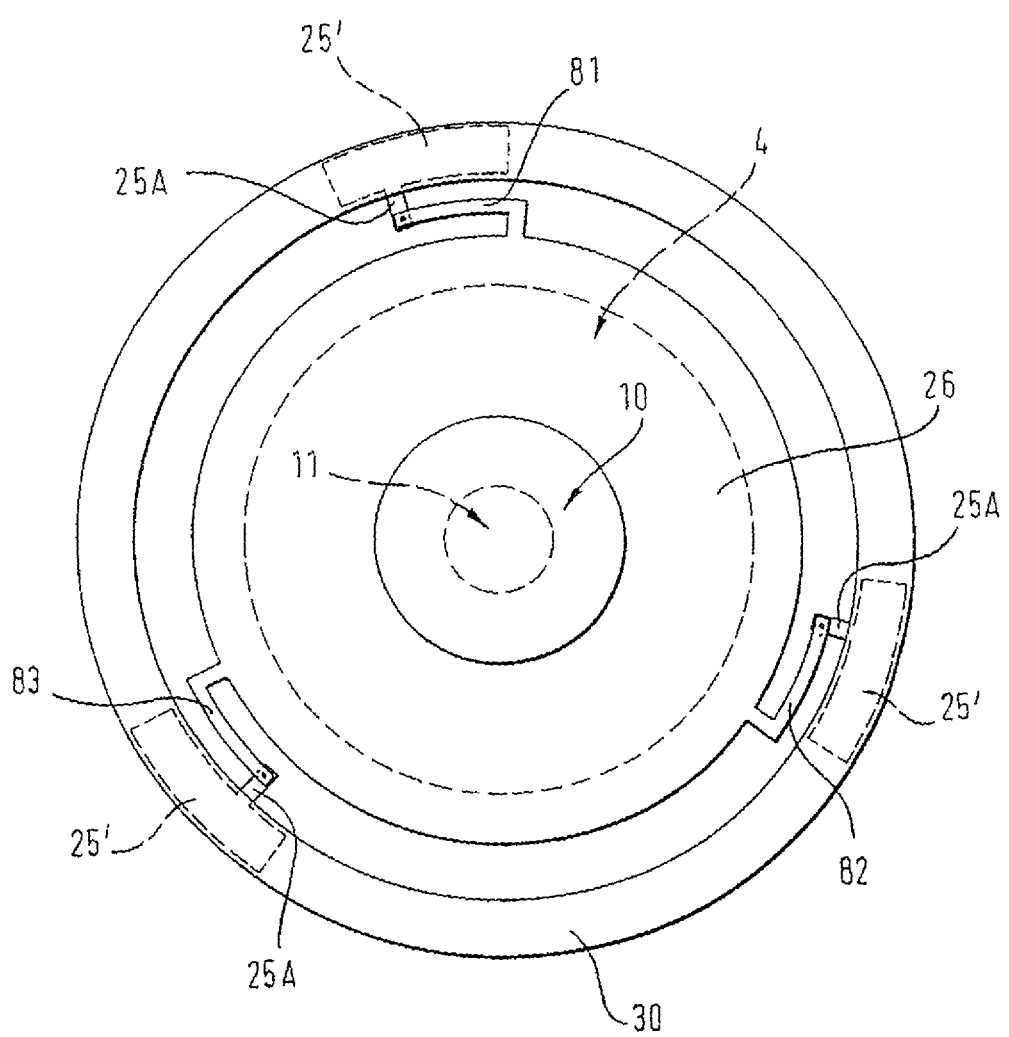

As shown in FIG. 9, if the outer section 25 of the substrate 3 is molded into a supporting body 30 of, for example a plastic material, or if another support structure 30 is provided, the outer section 25 may be provided in the form of outer partial sections 25'. In such a configuration the outer partial sections 25' are preferably first molded into or otherwise fixed to a supporting structure 30 which is, for example ring-shaped, to safely hold the partial sections 25' similar to the positions otherwise provided for each partial section 25' by being an integral part the outer annular section 25. It is preferred to manufacture the outer partial sections 25' separately and to fix the partial sections 25' to the supporting structure 30 in a separate manufacturing step. Thereafter, the inner section 26 and the resilient members 81, 82, 83, are respectively attached to the partial outer sections 25' by, for example welding the resilient elements 81, 82, 83 to the attachment parts 25A of the outer partial sections 25' protruding from said supporting body 30.

The invention claimed is:

1. A fluid dispersion device comprising:
   a substrate having an outer section and an inner section separated by a gap, the inner section of the substrate having an aperture;
   a dispersion element for generating a fluid droplet spray, wherein the dispersion element is positioned at the aperture to cover the aperture;
   an actuator affixed to the inner section and surrounding the aperture; and
   a plurality of resilient members, each resilient member extending across the gap between the inner section and the outer section of the substrate, the resilient members connecting the inner and outer sections in substantially the same plane, and resiliently coupling the inner section to the outer section.

2. A fluid dispersion device as defined in claim 1, wherein the aperture is positioned centrally in said inner section and is circularly shaped, and wherein the actuator is annularly shaped.

3. A fluid dispersion device as defined in claim 1, wherein the actuator comprises a piezoelectric element.

4. A fluid dispersion device as defined in claim 1, wherein the outer section and the inner section of the substrate are connected in a plane by the plurality of resilient members.

5. A fluid dispersion device as defined in claim 1, wherein the plurality of resilient members oscillate at or near resonance.

6. A fluid dispersion device as defined in claim 5, wherein the plurality of resilient members oscillate such that each of the resilient members has an oscillation node at an end attached to the outer section of the substrate.

7. A fluid dispersion device as defined in claim 1, wherein the outer section, the inner section and the plurality of resilient members are stainless steel.

8. A fluid dispersion device as defined in claim 1, wherein the plurality of resilient members are serpentine/meandering in form.

9. A fluid dispersion device as defined in claim 2, wherein the plurality of resilient members are aligned radially with respect to an axis of the aperture.

10. A fluid dispersion device as defined in claim 2, wherein the plurality of resilient members are aligned at an angle with respect to a radial line from the axis of the aperture.

11. A fluid dispersion device as defined in claim 1, wherein the inner section, the outer section and the resilient members are formed as a single solid.

12. A fluid dispersion device as defined in claim 1, wherein the inner section and the resilient members are formed as a single solid, wherein the outer section is provided with attachment sections and wherein the resilient members are attached to the attachment sections.

13. A fluid dispersion device as defined in claim 1, wherein the outer section and the resilient members are formed as a single solid, wherein the inner section is provided with attachment sections and wherein the resilient members are attached to the attachment sections.

14. A fluid dispersion device as defined in claim 1, wherein the outer section is provided with outer attachment sections and the inner section is provided with inner attachment sections, and wherein the resilient members are attached to the inner and outer attachment sections.

15. A fluid dispersion device as defined in claim 1, wherein the outer section comprises a plurality of outer partial sections which are positioned by a ring-shaped supporting structure.

16. A fluid dispersion device as defined in claim 1, wherein the outer section of the substrate is configured for attachment to a housing.

17. A fluid dispersion device as defined in claim 1 wherein at least one of said resilient members is adapted to carry an electrical signal for the actuator.

18. A fluid dispersion device as defined in claim 1, wherein the outer section and the inner section of the substrate are annularly shaped and wherein each resilient member has a length of at least 10% of a radius of the annularly shaped outer section.

* * * * *